United States Patent
Patrini et al.

(10) Patent No.: US 6,534,685 B1
(45) Date of Patent: Mar. 18, 2003

(54) LIQUID MIXTURE CONSISTING OF DIESEL GAS OILS AND OXYGENATED COMPOUNDS

(75) Inventors: Renata Patrini, Milan (IT); Mario Marchionna, Milan (IT)

(73) Assignee: Snamprogetti S.p.A., San Donato Milanese (IT)

( * ) Notice: Subject to any disclaimer, the term of this patent is extended or adjusted under 35 U.S.C. 154(b) by 0 days.

(21) Appl. No.: 09/478,402

(22) Filed: Jan. 6, 2000

(30) Foreign Application Priority Data

Jul. 22, 1999 (IT) .......................... MI99A1614

(51) Int. Cl.$^7$ .................. C07C 43/11; C07C 43/18; C07C 43/20; C10L 1/18; A01N 31/14; A61K 31/08

(52) U.S. Cl. .................. 568/613; 568/618; 568/606; 44/447; 44/448; 514/723

(58) Field of Search ................ 568/420, 606, 568/613, 618; 44/443, 444, 447, 448; 514/723

(56) References Cited

U.S. PATENT DOCUMENTS 2,449,469 A * 9/1948 Gresham et al. ............ 260/615
5,746,785 A * 5/1998 Moulton et al. ............. 44/443
5,959,156 A * 9/1999 Hagen et al. ............... 568/606

FOREIGN PATENT DOCUMENTS

RU 236897 * 8/1969
WO 86/03511 * 6/1986 ............. C10L/1/02

* cited by examiner

Primary Examiner—Samuel Barts
Assistant Examiner—Elvis O. Price
(74) Attorney, Agent, or Firm—Oblon, Spivak, McClelland, Maier & Neustadt, P.C.

(57) ABSTRACT

A liquid mixture is described having a cetane number higher than 40, characterized in that it consists of:

a typical diesel gas oil cut having a boiling point ranging from 150 to 380° C. and a density ranging from 0.76 to 0.935 g/ml at 15° C.;

one or more compounds selected from dialkyl-polyformals represented by the formula:

$$RO(CH_2O)_mR$$

wherein R is a $C_nH_{2n+1}$ alkyl chain
m is an integer equal to or greater than 2 and less than or equal to 6,
n is an integer ranging from 1 to 10,
wherein the concentration of said dialkyl-polyformals in the gas oil ranges from 1 to 20% by volume.

A process is also described for the production of dialkyl-polyformals, starting from alcohols and/or dialkylformals and formaldehyde in the presence of sulfonic acids optionally substituted.

10 Claims, 1 Drawing Sheet

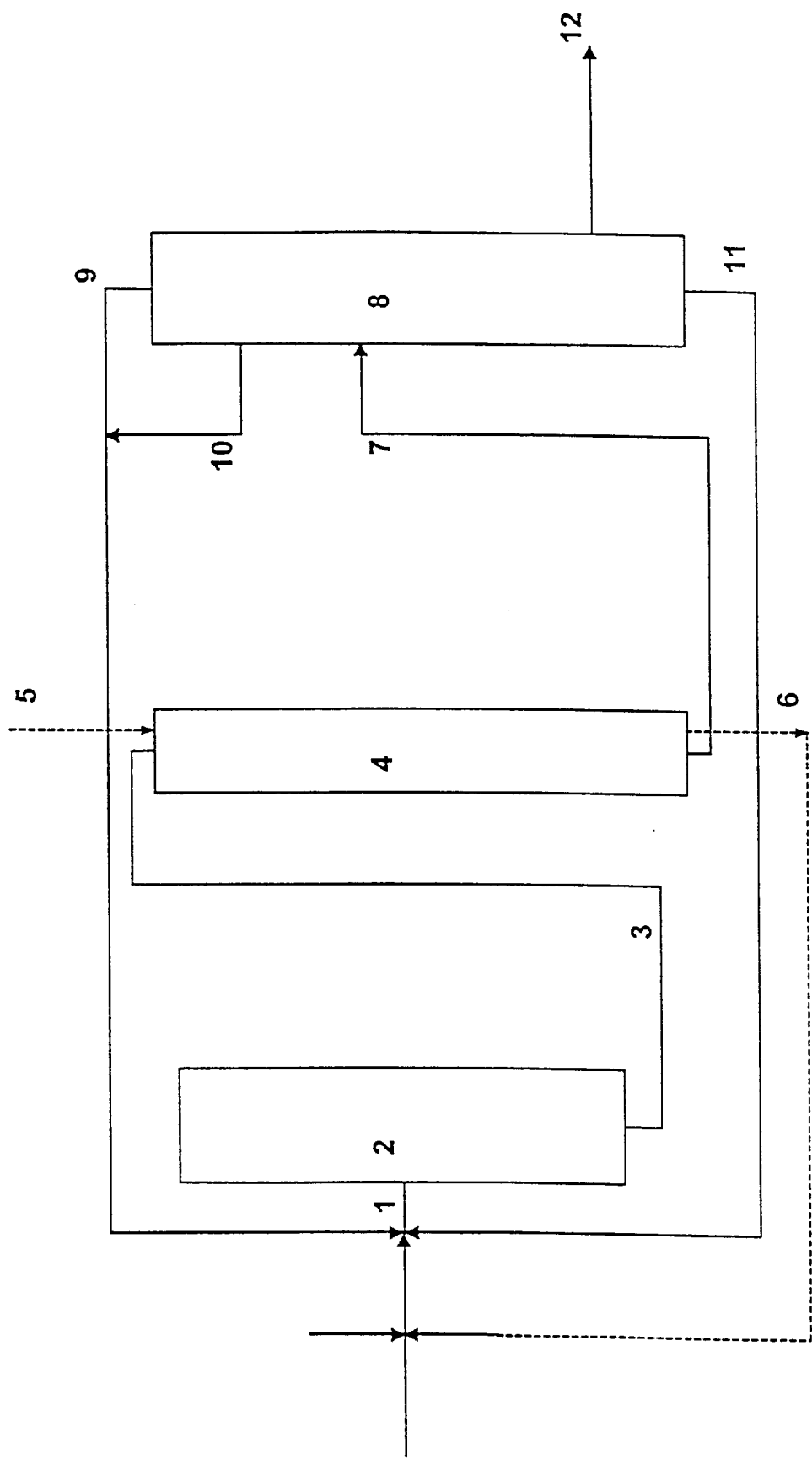

LIQUID MIXTURE CONSISTING OF DIESEL GAS OILS AND OXYGENATED COMPOUNDS

The present invention relates to a new liquid mixture consisting of diesel gas oils and certain oxygenated compounds, dialkyl-polyformals, which has increased cetane numbers with respect to conventional diesel gas oils.

The present invention also relates to a process for the selective production of said dialkyl-polyformals starting from alcohols and/or dialkylformals and formaldehyde using liquid acid catalysts.

Gas oil represents the heaviest part of medium distillates (200–360° C.). Both straight-run distillates and analogous cuts coming from conversion processes are joined in this fraction.

The main criteria for defining a gas oil are the boiling-point range and density range (0.760–0.935 at 15° C.). The main engine characteristics which determine the quality of a diesel gas oil are the combustion characteristics simulated by the cetane number.

Future fuel specifications in Europe seem to be directed towards diesels with an ever increasing cetane number, at the same time reducing the content of sulfur and polyaromatic hydrocarbons.

Whereas there are various process alternatives for improving the quality of gasolines, as far as gas oil is concerned, which historically is a less developed product than gasoline, there seem to be only two main methods for obtaining a high quality product in the refinery: either one has a good quality crude oil and therefore the gas oil obtained by distillation is also high quality (it only needs a relatively bland hydro-treatment) or it is necessary to resort to forced hydro-treatment and hydrocracking processes on the various fractions.

A third solution is to synthesize, or obtain from other sources, synthetic fuels or fuels of a natural origin which can form high quality components for reformulated gas oils: examples of the first category are Fischer-Tropsch gas oils and an example of the second category is "bio-diesel" deriving from seed oils.

Another group of particularly interesting compounds consists of linear ethers, with a total number of atoms$\geq 9$, which have a blending cetane number that is more than double the specific value of present gas oils and which have extremely interesting cold properties (Pecci, G. C., Clerici, M. G., Giavazzi F., Ancillotti, F., Marchionna, M., Patrini, R., IX Int. Symp. Alcohols Fuels, (1991), 1, 321; Giavazzi F., Terna, D., Patrini, R., Ancillotti, F., Pecci, G. C., Trerè, R., Benelli, M., IX Int. Symp. Alcohols Fuels, (1991) 1, 327).

On adding these ethers to a gas oil, all the properties of the latter are improved; not only is the cetane number considerably increased, but the cold properties are also improved, and in addition the content of aromatics and sulfur as well as the density are reduced as a result of the dilution (Marchionna, M., Patrini, R., Giavazzi, F., Pecci, G. C., Preprints 212th Nat. Meet. Am. Chem. Soc., Div. Petr. Chem, (1996), 41, 585).

From the point of view of environmental characteristics, these ethers have a positive effect on the reduction of emissions; in particular, the high cetane number allows a reduction in the emissions of hydrocarbons and CO, whereas the presence of oxygen in the molecule, accounts for a considerable reduction mainly in particulate emissions but also in those of $NO_x$.

Other activities of interest have been effected outside our research group. ARCO has carried out studies on the synergic effect of glycol ethers and alkyl peroxides as additives of gas oils. The results of ARCO research (Liotta, F. J., Jr. and Montalvo, D. M., SAE, Tech. Paper 932734, (1993); Nandi, M. K., Jacobs, D. C., Liotta, F. J., Jr. and Kesling, H. S., Jr., SAE, Tech. Paper 942019, (1994) on the use of glycol derivatives (at 5% in gas oil) are briefly summarized hereunder:

the addition of oxygen (as ether) causes a reduction in the particulate, but does not change its composition.

the $NO_x$ compounds do not decrease but rather increase slightly; if a cetane raiser of the peroxide type is added, however, also the $NO_x$ compounds decrease.

a fuel containing 31% of aromatics with the addition of oxygenated compounds and peroxides in the above proportion fully satisfies emission specifications in California and corresponds to a fuel containing only 15% of aromatics without oxygenated products.

Recently, moreover, it seems that ARCO Lyondell itself is ready to sell a reformulated gas oil to the Californian market ("EC Ultra Clean Diesel") which is very advanced for its properties (natural cetane number: 60; sulfur<15 ppm; aromatics<10% vol.). The composition of this gas oil is not known.

Various scientific papers have also recently appeared on the emissions of diesel engines which included glycol ethers, ethers and other oxygenated compounds (methylal) in the formulations of gas oils. In the last few years there has been a growing interest in gas oil components on the part of numerous petroleum companies and institutions.

A liquid mixture essentially consisting of gas oil and oxygenated components, has now been surprisingly found, which allows both the cetane number and oxygen percentage of gas oil to be increased.

The liquid mixture of the present invention, having a cetane number higher than 40, is characterized in that it consists of:

a typical diesel gas oil cut having a boiling point ranging from 150 to 380° C., preferably from 200 to 350° C., and a density ranging from 0.76 and 0.935 g/ml at 15° C.;

one or more compounds selected from dialkyl-polyformals represented by the formula $RO(CH_2O)_mR$, wherein R is a $C_nH_{2n+1}$ alkyl chain,
m is an integer equal to or greater than 2 and less than or equal to 6,
n is an integer ranging from 1 to 10, wherein the concentration of these dialkyl-polyformals in the gas oil ranges from 1 to 20%, preferably from 4 to 11% by volume.

More specifically, m is preferably equal to or greater than 3 and n is preferably equal to 1 or 2, more preferably m is equal to or greater than 3 and less than or equal to 5 and n is equal to 1.

Table A below indicates the blending cetane number data relating to this group of products determined by the addition of these components to a basic gas oil with a cetane number of 48.

These components are extremely interesting because, in addition to having a high cetane number and a high oxygen content (approx. 42–49%), which favours the reduction of the particulate, they originate from an inexpensive and widely available raw material.

TABLE A

| Compound | b.p. (° C.) | Blending cetane Nr. |
| --- | --- | --- |
| $CH_3O(CH_2O)_2CH_3$ | 105 | 63 |
| $CH_3O(CH_2O)_3CH_3$ | 156 | 78 |
| $CH_3O(CH_2O)_4CH_3$ | 202 | 90 |
| $CH_3O(CH_2O)_5CH_3$ | 242 | 100 |
| $CH_3CH_2O(CH_2O)_2CH_2CH_3$ | 140 | 77 |
| $CH_3CH_2O(CH_2O)_3CH_2CH_3$ | 185 | 89 |

Cetane raisers can be added to the typical diesel gas oil cut, used in the mixture of the invention, preferably in a concentration in the diesel gas oil of up to 1% by weight.

These cetane raisers can be selected from nitro-derivatives and dialkyl-peroxides.

The present invention also relates to a process for the selective production of dialkyl-polyformals starting from alcohols and/or dialkylformals and formaldehyde by the use of liquid acid catalysts; the process is characterized by both high yields and the particular recovery method of the catalyst from the product and its recycling.

The synthesis methods of dialkyl-polyformals $RO(CH_2O)_m R$ are the following:

$$2ROH + mCH_2O \rightarrow RO(CH_2O)_m R + H_2O \quad (1)$$

$$RO(CH_2O)R + (m-1)CH_2O \rightarrow RO(CH_2O)_m R \quad (2)$$

Both reactions take place with acid catalysis.

It is known that poly-oxymethylene-dimethylethers can be prepared starting from methanol and paraformaldehyde at high temperatures (Helv. Chim. Acta 8, 64 (1925), Ann. 474, 213, (1929); in the Dupont patent U.S. Pat. No. 2,449,469, the polyformals are prepared starting from paraformaldehyde and dialkylformal with sulfuric acid as catalyst (acid concentrations of about 0.1–2% by weight).

A process has now been surprisingly found which, operating also with very low concentrations of sulfonic acids, optionally substituted with halogens, as catalysts, allows high yields to polyformals to be obtained, starting from formaldehyde and alcohols and/or dialkylformals; this process also allows a simple and functional recovery of the catalyst from the reaction product and its recycling to the reaction environment.

The process, a further object of the present invention, for the production of dialkyl-polyformals represented by the formula $$RO(CH_2O)_m R,$$

wherein R is a $C_nH_{2n+1}$ alkyl chain, m and n are integers ranging from 1 to 10, carried out by means of reaction (1) and/or reaction (2) below $$2ROH + mCH_2O \rightarrow RO(CH_2O)_m R + H_2O \quad (1)$$

$$RO(CH_2O)R + (m-1)CH_2O \rightarrow RO(CH_2O)_m R \quad (2)$$

is characterized in that it uses, as catalysts, sulfonic acids or sulfonic acids substituted with halogens, operating at temperatures ranging from 50 to 200° C., preferably from 80 to 150° C., more preferably those enabling the formaldehyde (when used as paraformaldehyde or trioxane) to be dissolved in the reaction environment, and at pressures preferably ranging from 0.1 to 1 Mpa, more preferably those which guarantee temperatures sufficient for having the reagent (alcohol or dialkylformal) in liquid phase.

When operating under the conditions specified above, the reaction equilibrium is reached: the mixture obtained contains polyformals with m ranging from 2 to 5 with a selectivity of about 80–95%.

The concentration of the sulfonic acid or substituted sulfonic acid can vary within a wide range depending on the necessities and reagents present (type of formal and formaldehyde used): however it preferably ranges from 0.00001 to 0.01M.

Reaction (1) can be carried out with a molar ratio formaldehyde/alcohol greater than 0.1, preferably greater than 0.5, and with a molar ratio alcohol/sulfonic acids or alcohol/substituted sulfonic acids greater than 100, preferably greater than 500.

Reaction (2) can be carried out with a molar ratio formaldehyde/dialkylformal greater than 0.1 and with a molar ratio dialkylformal/sulfonic acids or dialkylformal/substituted sulfonic acids greater than 100, preferably greater than 500.

The formaldehyde used can be in aqueous solution or in methanol-aqueous solution, it can be in cyclic form (trioxane) or in polymer form (paraformaldehyde).

A wide variety of sulfonic acid catalysts can be used for this process: among these catalysts, the use of sulfonic acids substituted with fluorinated groups such as triflic acid or higher derivatives, is by far preferred.

A wide range of operating conditions can be used for producing polyformals in the desired selectivities using the object of the present invention. It is possible to operate in liquid phase or in liquid-vapor phase but operating conditions in liquid phase are preferred.

The process of the present invention can operate both under batch and continuous conditions; however it should be taken into account that the latter are much more advantageous in industrial practice. The reactor configuration may be optionally selected from isothermal, adiabatic, stirred, reactive distillation reactor, etc.

The process is preferably carried out, when reaction (1) is effected with m=1, as follows:

reaction (1) is effected first, wherein m is 1 (1a)

$$2ROH + CH_2O \rightarrow RO(CH_2O)R + H_2O \quad (1a)$$

by reacting the alcohol with the formaldehyde, using acid catalysts, and obtaining dialkyl-monoformal and water, and afterwards reaction (2) is effected, wherein m ranges from 1 to 10, by reacting the dialkyl-monoformal and formaldehyde, using a sulfonic acid or a sulfonic acid substituted with halogens (as described above).

The acid catalysts used for reaction (1a) can be selected from mineral acids, such as sulfuric acid, phosphoric acid, boron trifluoride, zeolites, sulfonated polymeric resins (for example Amberlyst 15 or Amberlyst 35), etc., or the same sulfonic acids or sulfonic acids substituted with halogens used for reaction (2).

This particular process can be optionally carried out in two separate steps, i.e. in a first step wherein the dialkyl monoformal obtained is separated from the water and reaction (2) is carried out in a second step to which the separated dialkyl-monoformal is sent.

Reaction (1a) can be carried out with a molar ratio formaldehyde/alcohol greater than 0.1, preferably greater than 0.5, and with a molar ratio dialkyl-monoformal/sulfonic acids greater than 100, preferably greater than 500, and reaction (2) with a molar ratio formaldehyde/dialkyl-polyformals greater than 0.1 and with a molar ratio dialkylformal/sulfonic acids greater than 100, preferably greater than 500.

The reaction is carried out under equilibrium conditions, the non-reacted dialkylformal is recycled to the reactor.

When n=1, the oligomer with m=2 and also the heavy products (m>6) recovered after distillation, can also be recycled. In the latter case, the heavy products, before being recycled to the reactor, can also be optionally treated with water.

The product containing part or the whole of the catalyst can be sent to a column containing silica gel, according to the disclosure of one of our previous patent applications for obtaining dialkyl ethers (IT-MI 97/A000754 of Feb. 4, 1997); operating as such, a completely deacidified product can be obtained without the use of bases which, by neutralizing the acid, produce salts which are difficult to dispose of.

The acid absorbed by the silica gel can, on the other hand, be easily extracted by elution with fresh dialkylformal (or also with the oligomer with m=2, when n=1) and the mixture of dialkylformals and acid obtained can be recycled together with the other streams to the reactor.

Operating as such, the catalyst losses are practically zero and the activity of catalyst in these passages remains unaltered.

An illustrative scheme of the process, for the specific case when m is equal to or greater than 3 and n is equal to 1, is provided in FIG. 1.

The stream (1), containing dialkylformals and formaldehyde optionally with fresh catalyst, is sent to a reactor (2) (preferably enameled to avoid corrosion phenomena). The reaction mixture containing both the products and the catalyst (3) leaving the reactor (2) is sent directly to the column (4) filled with silica gel where the mixture is purified of all the acid and traces of water. The latter components can be re-extracted with fresh dialkylformal (5) and/or with $CH_3O(CH_2O)_2CH_3$ and/or with $CH_3O(CH_2O)CH_3$ and recycled to the reactor (6). The neutralized reaction mixture (7) is sent to a distillation column (8) from where dialkylformal (9), the dimer (10) are obtained at the head and heavy products (11), recycled to the reactor (2), and the product (12), at the tail.

Some examples are provided hereunder for a better illustration of the invention, without limiting its scope in any way.

Equipment

Triflic acid dissolved in dialkylformal and paraformaldehyde are charged, in an inert atmosphere, into a 300 ml autoclave, under magnetic drag stirring.

The autoclave is closed and nitrogen is added until a pressure of about 2 atm is reached, and the autoclave is immersed in a thermostatic oil-bath regulated at the test temperature. The qualitative and quantitative composition of the reaction product is determined via gaschromatography using a standard product.

EXAMPLE 1

In this test dimethoxymethane (150 ml, 1.68 moles), paraformaldehyde (37.9 g, 1.26 moles) and triflic acid, $CF_3SO_3H$, (0.020 ml, 0.23 mmoles), were used. Operating under the conditions described above, (thermostatic bath at 120° C.) it was possible to obtain, after 40 minutes of reaction, a conversion of dimethoxymethane of 54.0%, a selectivity to polyformals ($2 \leq m \leq 5$) of 94.8% and to dimer (m=2) of 49.6%. The data are indicated in Table 1; the main by-product is methanol, which can be easily reconverted by a further addition of formaldehyde to dimethoxymethane (DMM) (Yield=DMM conversion x polyformal selectivity/100).

EXAMPLES 2–7

These examples show the effect of the variation in the concentration of the acid and demonstrate that, under these conditions (the tests were carried out at 115° C.), the best yields are obtained at acid concentrations of $1-2 \cdot 10^{-3}$ M. (See Tables 2 and 3)

EXAMPLES 8–12

These examples show the effect of the $CH_2O/DMM$ ratio at two different concentrations of triflic acid. The tests indicated in tables 4 and 5 demonstrate how different concentrations have different trends with variations in the $CH_2O/DMM$ ratio (See Tables 4 and 5).

EXAMPLE 13

This example shows that the system can also operate with methanol as reagent, in this case the main reaction product is dimethoxymethane (See Table 6).

TABLE 1

| Example | DMM/H$^+$ | CH$_2$O/DMM | Convers. (%) DMM | Selectivity CH$_3$O(CH$_2$O)$_m$CH$_3$ (%) | | | | | Yield (%) |
|---|---|---|---|---|---|---|---|---|---|
| | | | | m = 2 | m = 3 | m = 4 | m = 5 | Σ(2–5) | |
| 1 | 7420 | 0.74 | 54.0 | 49.6 | 28.4 | 11.9 | 4.7 | 94.8 | 51.2 |

TABLE 2

| Example | DMM/H$^+$ | CH$_2$O/DMM | [H$^+$] ×10$^{-3}$ | Conv. (%) DMM | Selectivity CH$_3$O(CH$_2$O)$_m$CH$_3$ (%) | | | | | Yield (%) |
|---|---|---|---|---|---|---|---|---|---|---|
| | | | | | m = 2 | m = 3 | m = 4 | m = 5 | Σ(2–5) | |
| 2 | 1150 | 1.5 | 10 | 54.7 | 49.6 | 25.3 | 8.5 | 2.7 | 86.0 | 47.0 |
| 3 | 640 | 1.5 | 18 | 50.3 | 53.8 | 23.7 | 6.5 | 1.7 | 85.7 | 43.1 |
| 4 | 320 | 1.5 | 36 | 41.2 | 57.5 | 19.0 | 3.9 | 0.8 | 81.2 | 33.5 |

Operating conditions:
Reaction duration 20 min.;
Temperature 115° C.

TABLE 3

| Example | DMM/H⁺ | CH₂O/DMM | [H⁺] ×10⁻³ | Conv. (%) DMM | Selectivity CH₃O(CH₂O)ₘCH₃ (%) m = 2 | m = 3 | m = 4 | m = 5 | Σ(2–5) | Yield (%) |
|---|---|---|---|---|---|---|---|---|---|---|
| 5 | 14550 | 0.78 | 0.8 | 9.3 | 23.8 | 10.5 | 3.6 | 1.4 | 39.3 | 3.7 |
| 6 | 7420 | 0.74 | 1.5 | 54.0 | 49.6 | 28.4 | 11.9 | 4.7 | 94.8 | 51.2 |
| 7 | 4000 | 0.74 | 2.8 | 52.6 | 48.7 | 25.5 | 10.3 | 4.1 | 88.6 | 46.6 |

Operating conditions:
Reaction duration 40 min.;
Temperature 115° C.

TABLE 4

| Example | DMM/H⁺ | CH₂O/DMM | [H⁺] ×10⁻³ | Conv. (%) DMM | Selectivity CH₃O(CH₂O)ₘCH₃ (%) m = 2 | m = 3 | m = 4 | m = 5 | Σ(2–5) | Yield (%) |
|---|---|---|---|---|---|---|---|---|---|---|
| 8 | 320 | 1.5 | 36 | 41.2 | 57.5 | 19.0 | 3.9 | 0.8 | 81.2 | 33.5 |
| 9 | 320 | 2.0 | 36 | 44.7 | 55.8 | 20.6 | 4.6 | 1.0 | 82.1 | 36.7 |

Operating conditions:
Reaction duration 20 min.;
Temperature 115° C.

TABLE 5

| Example | DMM/H⁺ | CH₂O/DMM | [H⁺] ×10⁻³ | Conv. (%) DMM | Selectivity CH₃O(CH₂O)ₘCH₃ (%) m = 2 | m = 3 | m = 4 | m = 5 | Σ(2–5) | Yield (%) |
|---|---|---|---|---|---|---|---|---|---|---|
| 10 | 7300 | 0.28 | 1.5 | 26.8 | 73.5 | 19.8 | 3.8 | 0.7 | 97.8 | 26.3 |
| 11 | 7300 | 0.52 | 1.5 | 51.3 | 50.9 | 25.2 | 9.5 | 3.5 | 89.1 | 45.7 |
| 12 | 7300 | 0.78 | 1.5 | 51.2 | 49.6 | 28.4 | 11.9 | 4.7 | 94.8 | 51.2 |

Operating conditions:
Reaction duration 40 min.;
Temperature 115° C.

TABLE 6

| Ex. | MeOH/H⁺ | CH₂O/ MeOH | [H⁺] ×10⁻³ | Conv. (%) MeOH | Conv. (%) CH₂O | Selectivity CH₃O(CH₂O)ₘCH₃ (%) m = 1 | m = 2 | m = 3 | m = 4 | m = 5 | Σ(2–5) | Yield (%) |
|---|---|---|---|---|---|---|---|---|---|---|---|---|
| 13 | 940 | 1.3 | 26 | 83 | 98 | 43.4 | 25.9 | 12.7 | 3.9 | 0.7 | 43.2 | 35.9 |

Operating conditions:
Reaction duration 20 min.;
Temperature 115° C.

What is claimed is:

1. A liquid mixture having a cetane number higher than 40 comprising:
   a typical diesel gas oil cut having a boiling point ranging from 150 to 380° C. and a density ranging from 0.76 to 0.935 g/ml at 15° C.;
   one or more compounds selected from dialkyl-polyformals represented by the formula $RO(CH_2O)_mR$, wherein R is a $C_nH_{2n+1}$ alkyl chain,
   m is an integer equal to or greater than 2 and less than or equal to 6,
   n is an integer ranging from 1 to 10,
   wherein the concentration of said dialkyl-polyformals in the gas oil ranges from 1 to 20% by volume.

2. The liquid mixture according to claim 1, wherein m is equal to or greater than 3 and n is equal to 1 or 2.

3. The liquid mixture according to claim 2, wherein m is equal to or greater than 3 and less than or equal to 5 and n is equal to 1.

4. The liquid mixture according to claim 1, wherein the dialkyl-polyformals are in a concentration in the gas oil in a quantity ranging from 4 to 11%.

5. The liquid mixture according to claim 1, wherein the typical diesel gas oil cut has a boiling point ranging from 200 to 350° C.

6. The liquid mixture according to claim 1, wherein cetane raisers are added to the typical diesel gas oil cut.

7. The liquid mixture according to claim 6, wherein the cetane raisers are in a concentration in the diesel gas oil of up to 1% by weight.

8. The liquid mixture according to claim 6, wherein the cetane raisers are selected from nitro-derivatives and dialkyl-peroxides.

9. A liquid mixture having a cetane number higher than 40 consisting essentially of:
   a typical diesel gas oil cut having a boiling point ranging from 150 to 380° C. and a density ranging from 0.76 to 0.935 g/ml at 15° C.;

one or more compounds selected from dialkyl-polyformals represented by the formula $RO(CH_2O)_m R$, wherein R is a $C_n H_{2n+1}$ alkyl chain, m is an integer equal to or greater than 2 and less than or equal to 6, n is an integer ranging from 1 to 10, wherein the concentration of said dialkyl-polyformals in the gas oil ranges from 1 to 20% by volume.

10. A liquid mixture having a cetane number higher than 40 consisting of:

a typical diesel gas oil cut having a boiling point ranging from 150 to 380° C. and a density ranging from 0.76 to 0.935 g/ml at 15° C.;

one or more compounds selected from dialkyl-polyformals represented by the formula $RO(CH_2O)_m R$, wherein R is a $C_n H_{2n+1}$ alkyl chain, m is an integer equal to or greater than 2 and less than or equal to 6, n is an integer ranging from 1 to 10, wherein the concentration of said dialkyl-polyformals in the gas oil ranges from 1 to 20% by volume.

* * * * *